US009821139B2

(12) United States Patent
Carleo

(10) Patent No.: US 9,821,139 B2
(45) Date of Patent: Nov. 21, 2017

(54) CATHETER HAVING INTERNAL HYDRATING FLUID STORAGE AND/OR CATHETER PACKAGE USING THE SAME AND METHOD OF MAKING AND/OR USING THE SAME

(75) Inventor: Steven Carleo, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1420 days.

(21) Appl. No.: 13/389,753

(22) PCT Filed: Aug. 28, 2009

(86) PCT No.: PCT/US2009/055389
§ 371 (c)(1),
(2), (4) Date: Mar. 20, 2012

(87) PCT Pub. No.: WO2011/019359
PCT Pub. Date: Feb. 17, 2011

(65) Prior Publication Data
US 2012/0168324 A1 Jul. 5, 2012

Related U.S. Application Data

(60) Provisional application No. 61/223,673, filed on Aug. 13, 2009.

(51) Int. Cl.
*A61B 19/02* (2006.01)
*A61M 27/00* (2006.01)
(Continued)

(52) U.S. Cl.
CPC ...... *A61M 25/0017* (2013.01); *A61M 25/002* (2013.01); *A61M 25/0014* (2013.01);
(Continued)

(58) Field of Classification Search
CPC .......... A61M 25/0014; A61M 25/0017; A61M 25/002; A61M 25/0045; A61M 25/0111;
(Continued)

(56) References Cited

U.S. PATENT DOCUMENTS 1,888,349 A 11/1932 Jacoby
2,912,981 A 11/1959 Keough
(Continued)

FOREIGN PATENT DOCUMENTS

CA 2770300 A1 2/2011
CA 2769026 C 4/2015
(Continued)

OTHER PUBLICATIONS

PCT/US2006/041633 filed Oct. 25, 2006 International Preliminary Report on Patentability dated Mar. 24, 2009.
(Continued)

*Primary Examiner* — Adam Marcetich
(74) *Attorney, Agent, or Firm* — Rutan & Tucker, LLP

(57) ABSTRACT

A catheter assembly (1) includes an inner member (12) having a proximal end (15), a distal end (13), and a lumen configured to store a hydrating fluid (28) An outer member (10) has a proximal end (19), a distal end (16), and a lumen configured to receive therein a portion of the inner member (12) The outer member (10) is movable relative to the inner member (12) at least one of, between a first position (FIG. 1) preventing fluid (28) from passing out of the at least one drainage opening (14) from within the lumen of the inner member (12) and a second position (FIG. 2) allowing fluid (28) to pass out of the at least one drainage opening (14) from within the lumen of the inner member (12).

14 Claims, 4 Drawing Sheets

(51) Int. Cl.
*A61M 25/00* (2006.01)
*A61M 25/01* (2006.01)

(52) U.S. Cl.
CPC ...... *A61M 25/0045* (2013.01); *A61M 25/0111* (2013.01); *A61M 2025/0056* (2013.01); *A61M 2025/0175* (2013.01)

(58) Field of Classification Search
CPC .. A61M 2025/0056; A61M 2025/0175; A61M 2025/0004; A61M 2025/0006; A61M 25/00; A61M 25/0009; A61M 2025/0062; A61M 25/0067; A61M 25/0074; A61M 25/0075; A61M 2210/1078; A61M 2210/1085; A61M 25/007; A61M 1/008; A61M 25/0023; A61M 2025/0024; A61M 2025/0025; A61M 2025/0681; B65D 21/086; B65D 2501/24547; B65D 25/44; B65D 47/061; B65D 47/063; A47G 21/18; A47G 21/189
See application file for complete search history.

(56) References Cited

U.S. PATENT DOCUMENTS

| | | | |
|---|---|---|---|
| 2,919,697 A | 1/1960 | Kim | |
| 3,173,566 A * | 3/1965 | Talbert | 215/229 |
| 3,344,791 A | 10/1967 | Foderick | |
| 3,556,294 A | 1/1971 | Walck et al. | |
| 3,556,874 A | 1/1971 | McClain | |
| 3,566,874 A | 3/1971 | Shepherd et al. | |
| 3,648,704 A | 3/1972 | Jackson | |
| 3,695,921 A | 10/1972 | Shepard et al. | |
| 3,699,964 A | 10/1972 | Ericson | |
| 3,726,281 A | 4/1973 | Norton et al. | |
| 3,794,042 A | 2/1974 | De Klotz et al. | |
| 3,802,987 A | 4/1974 | Noll | |
| 3,835,992 A | 9/1974 | Adams, IV | |
| 3,854,483 A | 12/1974 | Powers | |
| 3,861,395 A | 1/1975 | Taniguchi | |
| 3,894,540 A | 7/1975 | Bonner, Jr. | |
| 3,898,993 A | 8/1975 | Taniguchi | |
| 3,934,721 A | 1/1976 | Juster et al. | |
| 3,967,728 A | 7/1976 | Gordon et al. | |
| 4,026,296 A | 5/1977 | Stoy et al. | |
| 4,051,849 A | 10/1977 | Poncy et al. | |
| 4,055,682 A | 10/1977 | Merrill | |
| 4,062,363 A | 12/1977 | Bonner, Jr. | |
| 4,069,359 A | 1/1978 | DeMarse et al. | |
| 4,091,922 A | 5/1978 | Egler | |
| 4,140,127 A | 2/1979 | Cianci et al. | |
| 4,198,983 A | 4/1980 | Becker et al. | |
| 4,230,115 A | 10/1980 | Walz, Jr. et al. | |
| 4,245,639 A | 1/1981 | La Rosa | |
| 4,246,909 A | 1/1981 | Wu et al. | |
| 4,269,310 A | 5/1981 | Uson et al. | |
| 4,306,557 A | 12/1981 | North | |
| 4,350,161 A | 9/1982 | Davis, Jr. | |
| 4,366,901 A | 1/1983 | Short | |
| 4,392,848 A | 7/1983 | Lucas et al. | |
| 4,411,648 A | 10/1983 | Davis et al. | |
| 4,515,593 A | 5/1985 | Norton | |
| 4,517,971 A | 5/1985 | Sorbonne | |
| 4,560,382 A | 12/1985 | Isono et al. | |
| 4,571,241 A | 2/1986 | Christopher | |
| 4,585,666 A | 4/1986 | Lambert | |
| 4,597,765 A | 7/1986 | Klatt | |
| 4,607,746 A | 8/1986 | Stinnette | |
| 4,610,670 A | 9/1986 | Spencer | |
| 4,619,642 A | 10/1986 | Spencer | |
| 4,681,572 A | 7/1987 | Tokarz et al. | |
| 4,692,154 A | 9/1987 | Singery et al. | |
| 4,696,672 A | 9/1987 | Mochizuki et al. | |
| 4,704,102 A | 11/1987 | Guthery | |
| 4,723,946 A | 2/1988 | Kay | |
| 4,738,667 A | 4/1988 | Galloway | |
| 4,754,877 A | 7/1988 | Johansson et al. | |
| 4,759,753 A | 7/1988 | Schneider et al. | |
| 4,762,128 A | 8/1988 | Rosenbluth | |
| 4,773,901 A | 9/1988 | Norton | |
| 4,784,651 A | 11/1988 | Hickey et al. | |
| 4,811,847 A | 3/1989 | Reif et al. | |
| 4,838,876 A | 6/1989 | Wong et al. | |
| 4,886,508 A | 12/1989 | Washington | |
| 4,888,005 A | 12/1989 | Dingeman et al. | |
| 4,893,623 A | 1/1990 | Rosenbluth | |
| 4,932,938 A | 6/1990 | Goldberg et al. | |
| 4,957,487 A | 9/1990 | Gerow | |
| 4,997,426 A | 3/1991 | Dingeman et al. | |
| 5,007,897 A | 4/1991 | Kalb et al. | |
| 5,045,078 A | 9/1991 | Asta | |
| 5,077,352 A | 12/1991 | Elton | |
| 5,087,252 A | 2/1992 | Denard | |
| 5,098,379 A | 3/1992 | Conway et al. | |
| 5,100,396 A | 3/1992 | Zamierowski | |
| 5,137,671 A | 8/1992 | Conway et al. | |
| 5,147,341 A | 9/1992 | Starke et al. | |
| 5,174,290 A | 12/1992 | Fiddian-Green | |
| 5,179,174 A | 1/1993 | Elton | |
| 5,180,591 A | 1/1993 | Magruder et al. | |
| 5,186,172 A | 2/1993 | Fiddian-Green | |
| 5,188,596 A | 2/1993 | Condon et al. | |
| 5,201,724 A | 4/1993 | Hukins et al. | |
| 5,209,726 A | 5/1993 | Goosen | |
| 5,209,728 A | 5/1993 | Kraus et al. | |
| 5,224,953 A | 7/1993 | Morgentaler | |
| 5,226,530 A | 7/1993 | Golden | |
| 5,234,411 A | 8/1993 | Vaillancourt | |
| 5,236,422 A | 8/1993 | Eplett, Jr. | |
| 5,242,398 A | 9/1993 | Knoll et al. | |
| 5,242,428 A | 9/1993 | Palestrant | |
| 5,261,896 A | 11/1993 | Conway et al. | |
| 5,269,755 A | 12/1993 | Bodicky | |
| 5,269,770 A | 12/1993 | Conway et al. | |
| 5,282,795 A | 2/1994 | Finney | |
| 5,352,182 A | 10/1994 | Kalb et al. | |
| 5,360,402 A | 11/1994 | Conway et al. | |
| 5,370,899 A | 12/1994 | Conway et al. | |
| 5,415,165 A | 5/1995 | Fiddian-Green | |
| 5,417,666 A | 5/1995 | Coulter | |
| 5,433,713 A | 7/1995 | Trotta | |
| 5,445,626 A | 8/1995 | Gigante et al. | |
| 5,447,231 A | 9/1995 | Kastenhofer | |
| 5,454,798 A | 10/1995 | Kubalak et al. | |
| 5,456,251 A | 10/1995 | Fiddian-Green | |
| 5,466,229 A | 11/1995 | Elson et al. | |
| 5,476,434 A | 12/1995 | Kalb et al. | |
| 5,482,740 A | 1/1996 | Conway et al. | |
| 5,501,669 A | 3/1996 | Conway et al. | |
| 5,509,889 A | 4/1996 | Kalb et al. | |
| 5,514,112 A | 5/1996 | Chu et al. | |
| 5,520,636 A | 5/1996 | Korth et al. | |
| 5,531,715 A | 7/1996 | Engelson et al. | |
| 5,531,717 A | 7/1996 | Roberto et al. | |
| 5,536,258 A | 7/1996 | Folden | |
| 5,558,900 A | 9/1996 | Fan et al. | |
| 5,569,219 A | 10/1996 | Hakki et al. | |
| 5,582,599 A | 12/1996 | Daneshvar | |
| 5,591,292 A | 1/1997 | Blomqvist | |
| 5,599,321 A | 2/1997 | Conway et al. | |
| 5,601,537 A | 2/1997 | Frassica | |
| 5,607,417 A | 3/1997 | Batich et al. | |
| 5,616,126 A | 4/1997 | Malekmehr et al. | |
| 5,624,395 A | 4/1997 | Mikhail et al. | |
| 5,653,700 A | 8/1997 | Byrne et al. | |
| 5,670,111 A | 9/1997 | Conway et al. | |
| 5,688,516 A | 11/1997 | Raad et al. | |
| 5,704,353 A | 1/1998 | Kalb et al. | |
| 5,707,357 A | 1/1998 | Mikhail et al. | |
| 5,711,841 A | 1/1998 | Jaker | |
| 5,749,826 A | 5/1998 | Faulkner | |
| 5,779,670 A | 7/1998 | Bidwell et al. | |
| 5,782,808 A | 7/1998 | Folden | |

(56) References Cited

U.S. PATENT DOCUMENTS

| | | |
|---|---|---|
| 5,785,694 A | 7/1998 | Cohen et al. |
| 5,788,687 A | 8/1998 | Batich et al. |
| 5,800,339 A | 9/1998 | Salama |
| 5,817,067 A | 10/1998 | Tsukada et al. |
| 5,820,583 A | 10/1998 | Demopulos et al. |
| 5,840,151 A | 11/1998 | Munsch |
| 5,848,691 A | 12/1998 | Morris et al. |
| 5,853,518 A | 12/1998 | Utas et al. |
| 5,871,475 A | 2/1999 | Frassica |
| 5,895,374 A | 4/1999 | Rodsten et al. |
| 5,897,535 A | 4/1999 | Feliziani et al. |
| 5,941,856 A | 8/1999 | Kovacs et al. |
| 5,971,954 A | 10/1999 | Conway et al. |
| 5,980,483 A | 11/1999 | Dimitri et al. |
| 5,989,230 A | 11/1999 | Frassica |
| 6,004,305 A | 12/1999 | Hursman et al. |
| 6,007,521 A | 12/1999 | Bidwell et al. |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,090,075 A | 7/2000 | House |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,210,394 B1 | 4/2001 | Demopulos et al. |
| 6,217,569 B1 | 4/2001 | Fiore |
| 6,221,056 B1 | 4/2001 | Silverman |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,261,279 B1 | 7/2001 | Demopulos et al. |
| 6,293,923 B1 | 9/2001 | Yachia et al. |
| 6,299,598 B1 | 10/2001 | Bander |
| 6,306,422 B1 | 10/2001 | Batich et al. |
| 6,329,488 B1 | 12/2001 | Terry et al. |
| 6,340,359 B1 | 1/2002 | Silverman |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Israelsson et al. |
| 6,458,867 B1 | 10/2002 | Wang et al. |
| 6,468,245 B2 | 10/2002 | Alexandersen et al. |
| 6,485,476 B1 | 11/2002 | von Dyck et al. |
| 6,544,240 B1 | 4/2003 | Borodulin et al. |
| 6,578,709 B1 | 6/2003 | Kavanagh et al. |
| 6,582,401 B1 | 6/2003 | Windheuser et al. |
| 6,602,244 B2 | 8/2003 | Kavanagh et al. |
| 6,613,342 B2 | 9/2003 | Aoki |
| 6,626,888 B1 | 9/2003 | Conway et al. |
| 6,629,969 B2 | 10/2003 | Chan et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,695,831 B1 | 2/2004 | Tsukada et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,730,113 B2 | 5/2004 | Eckhardt et al. |
| 6,736,805 B2 | 5/2004 | Israelsson et al. |
| 6,746,421 B2 | 6/2004 | Yachia et al. |
| 6,783,520 B1 | 8/2004 | Candray et al. |
| D496,266 S | 9/2004 | Nestenborg et al. |
| 6,824,532 B2 | 11/2004 | Gillis et al. |
| 6,835,183 B2 | 12/2004 | Lennox et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,887,230 B2 | 5/2005 | Kubalak et al. |
| 6,889,740 B1 | 5/2005 | Globensky et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |
| 7,001,370 B2 | 2/2006 | Kubalak et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,195,608 B2 | 3/2007 | Burnett |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-tine et al. |
| 7,311,690 B2 | 12/2007 | Burnett |
| 7,311,698 B2 | 12/2007 | Tanghoj et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| 7,662,146 B2 | 2/2010 | House |
| 7,682,353 B2 | 3/2010 | Tanghoj et al. |
| 7,770,726 B2 | 8/2010 | Murray et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,066,693 B2 | 11/2011 | Tanghoj et al. |
| 8,177,774 B2 | 5/2012 | House |
| 8,181,778 B1 | 5/2012 | Van Groningen et al. |
| 8,205,745 B2 | 6/2012 | Murray et al. |
| 8,328,792 B2 | 12/2012 | Nishtala et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,998,882 B2 | 4/2015 | Knapp et al. |
| 9,033,149 B2 | 5/2015 | Terry |
| 9,114,227 B2 | 8/2015 | Blanchard |
| 9,694,113 B2 | 7/2017 | Knapp et al. |
| 2001/0001443 A1 | 5/2001 | Kayerod et al. |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |

(56) References Cited

U.S. PATENT DOCUMENTS

| | | |
|---|---|---|
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0130646 A1 | 7/2003 | Kubalak et al. |
| 2003/0132307 A1* | 7/2003 | Park ................................ 239/33 |
| 2003/0135200 A1 | 7/2003 | Byrne |
| 2003/0163079 A1 | 8/2003 | Burnett |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0116551 A1 | 6/2004 | Terry |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0243104 A1 | 12/2004 | Seddon |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0283136 A1 | 12/2005 | Skarda |
| 2006/0025753 A1 | 2/2006 | Kubalak et al. |
| 2006/0027854 A1 | 2/2006 | Kim et al. |
| 2006/0030864 A1 | 2/2006 | Kennedy et al. |
| 2006/0036208 A1 | 2/2006 | Burnett |
| 2006/0041246 A1 | 2/2006 | Provost-tine et al. |
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0163097 A1 | 7/2006 | Murray et al. |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0196783 A1 | 9/2006 | Bruun et al. |
| 2006/0200079 A1 | 9/2006 | Magnusson |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005041 A1 | 1/2007 | Frassica et al. |
| 2007/0010798 A1 | 1/2007 | Stoller et al. |
| 2007/0016169 A1 | 1/2007 | Utas et al. |
| 2007/0049879 A1 | 3/2007 | Gutierrez |
| 2007/0066963 A1 | 3/2007 | Tanghoj |
| 2007/0106233 A1 | 5/2007 | Huang et al. |
| 2007/0112327 A1 | 5/2007 | Yun et al. |
| 2007/0149929 A1 | 6/2007 | Utas et al. |
| 2007/0197957 A1 | 8/2007 | Hunter et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2008/0006554 A1 | 1/2008 | Duffy et al. |
| 2008/0015518 A1 | 1/2008 | Huang et al. |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1* | 2/2008 | Ziegler et al. ................. 424/490 |
| 2008/0051762 A1 | 2/2008 | Tsukada et al. |
| 2008/0051763 A1 | 2/2008 | Frojd |
| 2008/0077099 A1 | 3/2008 | House |
| 2008/0082051 A1 | 4/2008 | Miller et al. |
| 2008/0085949 A1 | 4/2008 | McGhee |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172042 A1 | 7/2008 | House |
| 2008/0179208 A1 | 7/2008 | Murray et al. |
| 2008/0200907 A1 | 8/2008 | Nestenborg |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2009/0024111 A1 | 1/2009 | Borodulin et al. |
| 2009/0048537 A1 | 2/2009 | Lydon et al. |
| 2009/0054876 A1* | 2/2009 | Borodulin et al. ............ 604/544 |
| 2009/0065605 A1* | 3/2009 | Roche et al. .................... 239/33 |
| 2009/0071851 A1 | 3/2009 | Maki et al. |
| 2009/0131917 A1 | 5/2009 | Kavanagh et al. |
| 2009/0137985 A1* | 5/2009 | Tanghoej et al. ............ 604/544 |
| 2009/0137986 A1 | 5/2009 | Golden et al. |
| 2009/0149837 A1 | 6/2009 | Tanghoj et al. |
| 2009/0156882 A1* | 6/2009 | Chi Sing et al. ................ 600/7 |
| 2009/0200187 A1 | 8/2009 | Nestenborg et al. |

(56) References Cited

U.S. PATENT DOCUMENTS

| | | |
|---|---|---|
| 2009/0299334 A1 | 12/2009 | Nishtala et al. |
| 2009/0318900 A1* | 12/2009 | Tanghoj et al. ............... 604/544 |
| 2010/0198195 A1 | 8/2010 | Nishtala et al. |
| 2010/0263327 A1 | 10/2010 | Murray et al. |
| 2010/0324540 A1* | 12/2010 | Paulen et al. ................. 604/544 |
| 2011/0028943 A1 | 2/2011 | Lawson et al. |
| 2011/0056852 A1 | 3/2011 | Frojd |
| 2011/0114520 A1 | 5/2011 | Matthison-Hansen |
| 2011/0127186 A1 | 6/2011 | Enns et al. |
| 2011/0137296 A1 | 6/2011 | Tanghoj |
| 2011/0184386 A1 | 7/2011 | House |
| 2012/0179102 A1 | 7/2012 | Blanchard et al. |
| 2012/0316515 A1 | 12/2012 | Terry |
| 2013/0006226 A1 | 1/2013 | Hong et al. |
| 2013/0048516 A1 | 2/2013 | Nishtala et al. |
| 2013/0153446 A1 | 6/2013 | Utas et al. |
| 2013/0186778 A1 | 7/2013 | Terry |
| 2014/0262859 A1 | 9/2014 | Knapp et al. |
| 2015/0238726 A1 | 8/2015 | Terry |
| 2015/0273116 A1 | 10/2015 | Knapp et al. |

FOREIGN PATENT DOCUMENTS

| | | |
|---|---|---|
| CN | 102939127 A | 2/2013 |
| DE | 10213411 A1 | 10/2003 |
| EP | 0217771 | 4/1987 |
| EP | 247559 A1 | 12/1987 |
| EP | 0252918 A1 | 1/1988 |
| EP | 0479935 A1 | 4/1992 |
| EP | 0677299 | 10/1995 |
| EP | 0699086 A1 | 3/1996 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1175355 A1 | 1/2002 |
| EP | 1237615 A1 | 9/2002 |
| EP | 1245205 | 10/2002 |
| EP | 1308146 | 5/2003 |
| EP | 1406690 A2 | 4/2004 |
| EP | 1409060 A2 | 4/2004 |
| EP | 1420846 A1 | 5/2004 |
| EP | 1420847 A2 | 5/2004 |
| EP | 1427467 A2 | 6/2004 |
| EP | 1498151 | 1/2005 |
| EP | 1629860 | 3/2006 |
| EP | 1641510 A1 | 4/2006 |
| EP | 1642610 | 4/2006 |
| EP | 1642611 | 4/2006 |
| EP | 2060296 A1 | 5/2009 |
| EP | 2459264 A1 | 6/2012 |
| EP | 2464411 A1 | 6/2012 |
| EP | 2515988 A1 | 10/2012 |
| EP | 2542291 A1 | 1/2013 |
| FR | 2731345 A1 | 9/1996 |
| GB | 2284764 | 6/1995 |
| GB | 2319507 | 5/1998 |
| JP | 2001-500414 A | 1/2001 |
| JP | 2007-501656 A | 2/2007 |
| JP | 2013-500125 | 1/2013 |
| JP | 2013-515572 | 5/2013 |
| WO | 8401296 A1 | 4/1984 |
| WO | 8606284 | 11/1986 |
| WO | 9105577 A1 | 5/1991 |
| WO | 9416747 A1 | 8/1994 |
| WO | 9638192 A1 | 12/1996 |
| WO | 9726937 | 7/1997 |
| WO | 9741811 | 11/1997 |
| WO | 9806642 | 2/1998 |
| WO | 9811932 | 3/1998 |
| WO | 9819729 | 5/1998 |
| WO | 9930761 A1 | 6/1999 |
| WO | 0016843 | 3/2000 |
| WO | 0047494 | 8/2000 |
| WO | 0143807 | 6/2001 |
| WO | 0152763 | 7/2001 |
| WO | 0193935 | 12/2001 |
| WO | 0236192 | 5/2002 |
| WO | 03002177 | 1/2003 |
| WO | 03002178 | 1/2003 |
| WO | 03008028 | 1/2003 |
| WO | 03008029 | 1/2003 |
| WO | 03064279 A1 | 8/2003 |
| WO | 03092779 | 11/2003 |
| WO | 2004030722 | 4/2004 |
| WO | 2004045696 | 6/2004 |
| WO | 2004045696 A1 | 6/2004 |
| WO | 2004050155 | 6/2004 |
| WO | 2004052440 | 6/2004 |
| WO | 2004056414 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2007/050685 A2 | 5/2007 |
| WO | 2007050685 | 5/2007 |
| WO | 2009012336 A1 | 1/2009 |
| WO | 2007050685 A3 | 4/2009 |
| WO | 2011014201 A1 | 2/2011 |
| WO | 2011019359 A1 | 2/2011 |
| WO | 2011063816 A1 | 6/2011 |
| WO | 2011079129 A1 | 6/2011 |
| WO | 2011109393 A1 | 9/2011 |
| WO | 2014165046 A1 | 10/2014 |

OTHER PUBLICATIONS

PCT/US2006/041633 filed Oct. 25, 2006 Search Report dated Aug. 12, 2008.

PCT/US2006/041633 filed Oct. 25, 2006 Written Opinion dated Aug. 12, 2008.

PCT/US2009/055395 filed Aug. 28, 2009 International Preliminary Report on Patentability dated Jan. 31, 2012.

PCT/US2009/055395 filed Aug. 28, 2009 International Search Report dated Oct. 15, 2009.

PCT/US2009/055395 filed Aug. 28, 2009 Written Opinion dated Oct. 15, 2009.

PCT/US2010/061597 filed Dec. 21, 2010 International Preliminary Report on Patentability dated Jun. 26, 2012 and Written Opinion dated Feb. 28, 2011.

PCT/US2010/061597 filed Dec. 21, 2010 International Search Report dated Feb. 28, 2011.

PCT/US2011/026681 filed Mar. 1, 2011 International Preliminary Report on Patentability dated Sep. 4, 2012.

PCT/US2011/026681 filed Mar. 1, 2011 International Search Report dated Apr. 27, 2011.

PCT/US2011/026681 filed Mar. 1, 2011 Written Opinion dated Apr. 27, 2011.

U.S. Appl. No. 12/091,916, filed Feb. 2, 2009 Final Office Action dated Sep. 22, 2011.

U.S. Appl. No. 12/091,916, filed Feb. 2, 2009 Non-Final Office Action dated May 10, 2011.

U.S. Appl. No. 12/091,916, filed Feb. 2, 2009 Non-Final Office Action dated Nov. 24, 2010.

U.S. Appl. No. 12/091,916, filed Feb. 2, 2009 Notice of Allowance dated Aug. 17, 2012.

U.S. Appl. No. 13/387,447, filed Mar. 22, 2012 Non-Final Office Action dated Jan. 15, 2013.

PCT/US2009/055389 filed Aug. 28, 2009 International Search Report dated Oct. 20, 2009.

(56) References Cited

OTHER PUBLICATIONS

PCT/US2009/055389 filed Aug. 28, 2009 Written Opinion dated Oct. 20, 2009.
CA 2,769,026 filed Jan. 24, 2012 First Examination Report dated Nov. 4, 2013.
CN 201080058895.4 filed Jun. 21, 2012 First Office Action dated Feb. 27, 2014.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 11751198.0 filed Sep. 28, 2012 Exam Report dated Feb. 7, 2014.
EP 11751198.0 filed Sep. 28, 2012 extended European search report dated Jul. 9, 2013.
JP 2012-546157 filed Jun. 12, 2012 First Office Action dated Sep. 16, 2014.
PCT/US2014/024231 filed Mar. 12, 2014 International Search Report and Written Opinion dated Jul. 10, 2014.
U.S. Appl. No. 13/387,447, filed Mar. 22, 2012 Advisory Action dated Feb. 27, 2014.
U.S. Appl. No. 13/387,447, filed Mar. 22, 2012 Final Office Action dated Dec. 11, 2013.
U.S. Appl. No. 13/387,447, filed Mar. 22, 2012 Final Office Action dated Oct. 31, 2014.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/582,698, filed Sep. 4, 2012 Non-Final Office Action dated Sep. 24, 2014.
U.S. Appl. No. 13/662,278, filed Oct. 26, 2012 Non-Final Office Action dated Sep. 12, 2014.
U.S. Appl. No. 13/802,095, filed Mar. 13, 2013 Non-Final Office Action dated Aug. 15, 2014.
"Tripartite Biocompatibility Guidance for Medical Devices," DSMA (Apr. 24, 1987).
Norton, J.A. et al., Surgery: Basic Science and Clinical Evidence Springer, 2nd ed., 2008, p. 281.
U.S. Appl. No. 13/516,660, filed Aug. 27, 2012 Final Office Action dated Jun. 29, 2016.
U.S. Appl. No. 13/662,278, filed Oct. 26, 2012 Non-Final Office Action dated Jul. 7, 2016.
CN 201080058895.4 filed Jun. 21, 2012 Second Office Action dated Nov. 3, 2014.
CN 201080058895.4 filed Jun. 21, 2012 Third Office Action dated May 4, 2015.
EP 10840071.4 filed Jul. 4, 2012 Office Action dated Jul. 9, 2015.
U.S. Appl. No. 13/387,447, filed Mar. 22, 2012 Final Office Action dated Oct. 5, 2015.
U.S. Appl. No. 13/387,447, filed Mar. 22, 2012 Non-Final Office Action dated Mar. 12, 2015.
U.S. Appl. No. 13/662,278, filed Oct. 26, 2012 Final Office Action dated Feb. 20, 2015.
U.S. Appl. No. 13/802,095, filed Mar. 13, 2013 Notice of Allowance dated Nov. 28, 2014.
BR PI 0506836-3 filed Jan. 18, 2005, Technical Report dated Jul. 28, 2015.
JP 2012-546157 filed Jun. 12, 2012 Decision of Rejection dated Aug. 21, 2015.
U.S. Appl. No. 13/662,278, filed Oct. 26, 2012 Non-Final Office Action dated Sep. 17, 2015.
U.S. Appl. No. 13/516,660, filed Aug. 27, 2012 Non-Final Office Action dated Mar. 8, 2016.
CN 201480013064.3 filed Sep. 8, 2015 Office Action dated Oct. 10, 2016.
U.S. Appl. No. 13/387,447, filed Mar. 22, 2012 Examiner's Answer dated Oct. 5, 2016.
U.S. Appl. No. 13/662,278, filed Oct. 26, 2012 Final Office Action dated Oct. 19, 2016.
U.S. Appl. No. 14/707,954, filed May 8, 2015 Non-Final Office Action dated Dec. 1, 2016.
CN 201480013064.3 filed Sep. 8, 2015 Office Action dated Jun. 29, 2017.
EP 10840071.4 filed Jul. 4, 2012 Notice of Opposition dated Apr. 24, 2017.
EP 14779919.1 filed Sep. 10, 2015 Office Action dated Jul. 4, 2017.
EP 16171279.9 filed May 25, 2016 Intent to Grant, dated Jun. 13, 2017.
U.S. 13/662,278, filed Oct. 26, 2012 Examiner's Answer dated Jun. 2, 2017.

* cited by examiner

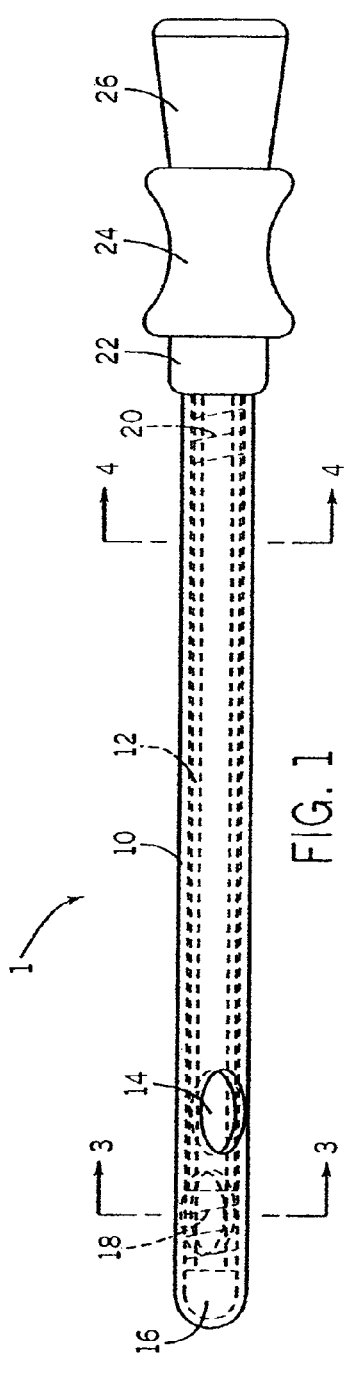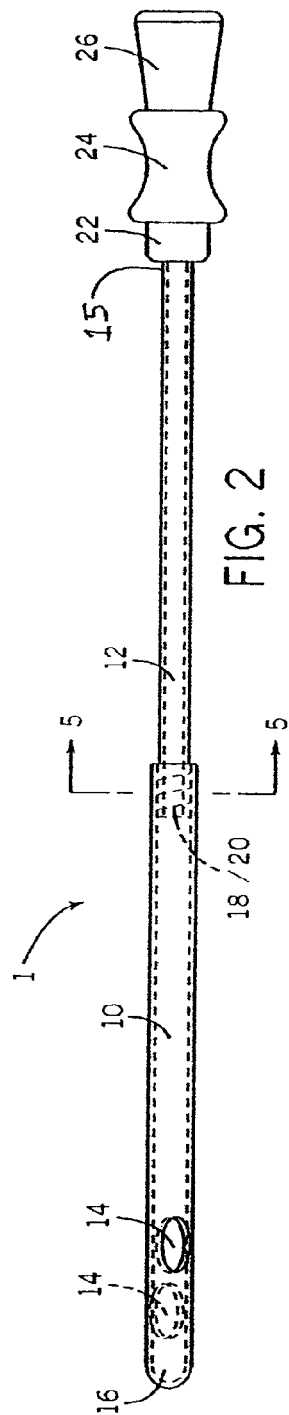

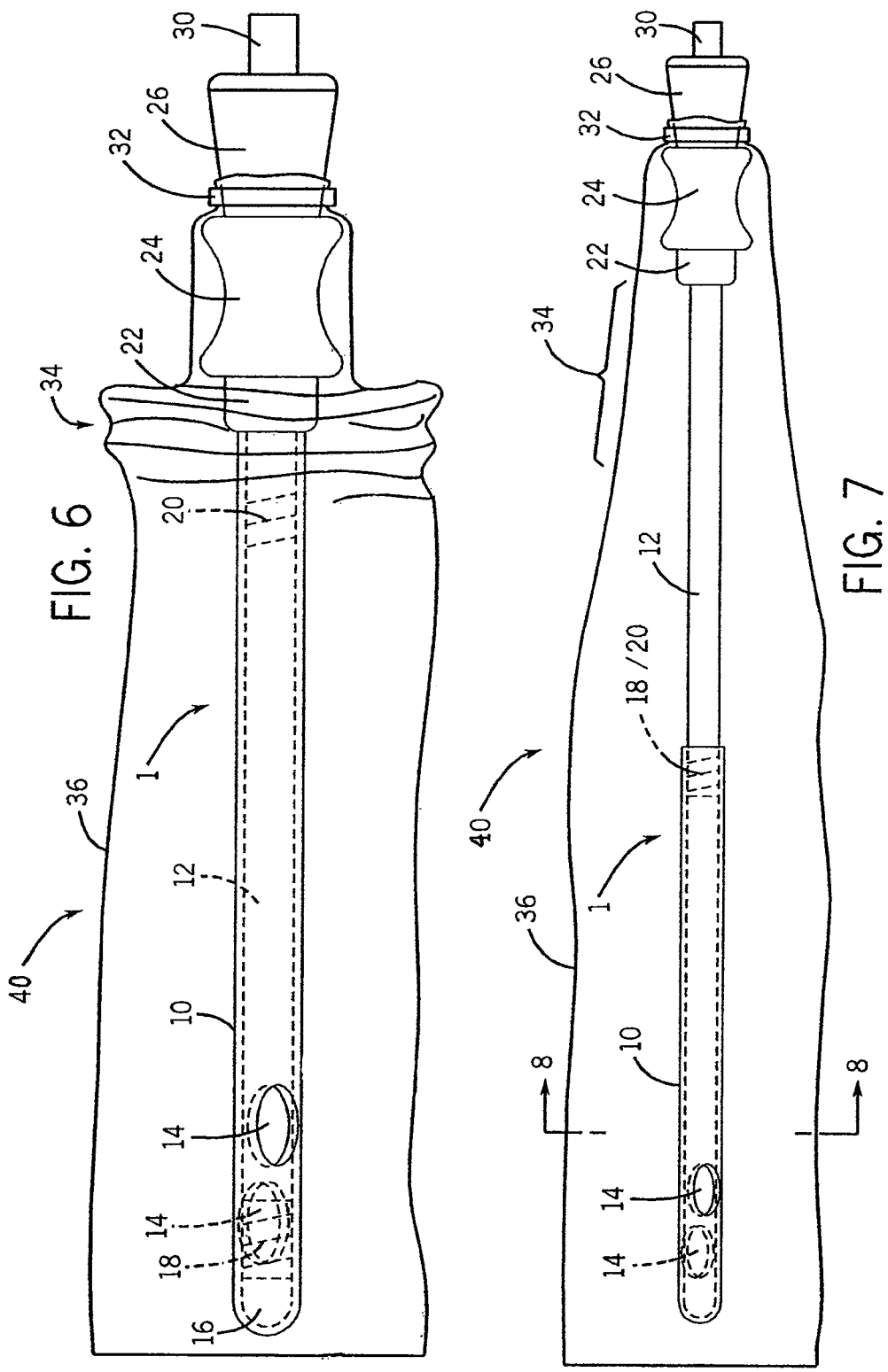

CATHETER HAVING INTERNAL HYDRATING FLUID STORAGE AND/OR CATHETER PACKAGE USING THE SAME AND METHOD OF MAKING AND/OR USING THE SAME

CROSS REFERENCE TO RELATED APPLICATIONS

This application is a U.S. national stage application under 35 U.S.C. §371 of International Application No. PCT/US2009/055389, filed Aug. 28, 2009, claiming priority to U.S. Provisional Application No. 61/223,673, filed Aug. 13, 2009, each of which is incorporated by reference in its entirety into this application.

STATEMENT CONCERNING GOVERNMENT INTEREST

Not applicable.

BACKGROUND OF THE INVENTION

Intermittent catheterization is a sterile process of draining urine from the bladder when normal draining is impossible or difficult. Proper intermittent catheter use reduces the risk of urinary tract infections and kidney damage. Intermittent catheters come in many different sizes and lengths to fit the body. Some catheters are also available pre-lubricated.

Intermittent catheterization is generally performed a minimum of four times a day by the patient or a care giver. The genital area near the urethral opening is wiped with an antiseptic agent, such as iodine. A lubricant may then be used to facilitate the entry of the catheter into the urethra. A topical local anesthetic may also be applied to numb the urethral opening during the procedure. One end of the catheter is placed in a container, and the other end is inserted into and guided up the urethra and into the bladder until urine flow begins.

When urine flow stops, the catheter may be re-positioned, moved or rotated. The patient may also be made to change positions to ensure that all urine has emptied from the bladder. The catheter may then be withdrawn, cleaned, and sterilized for the next use. Recommended cleaning practices vary, from the use of soap and water, to submersion in boiling water or a disinfectant solution. Some patients prefer to use a new catheter with each insertion or catheterization.

Intermittent catheters are generally catheters or tubes having a rounded, atraumatic distal tip that is inserted into the bladder of a patient. A molded funnel is typically connected to a distal end that remains outside the body of the patient or user. The distal tip may include slots or openings on the shaft to facilitate drainage of urine therefrom once the tip is positioned inside the bladder.

Pre-wetted intermittent catheters are intermittent catheters having a highly lubricious coating on an outer surface thereof, which are packaged or otherwise brought into contact with fluid in order to provide a catheter with a slippery outer surface to facilitate insertion into the patient or user.

Existing pre-wetted intermittent catheters fall into three broad categories. In a first type, the catheter is packaged in a dry environment, but it contains a lubricious coating that requires a wetting fluid in order to become hydrated. The wetting fluid is obtained from an external source by the user (e.g., sink, bottled water, etc.), and the catheter is positioned within the wetting fluid for a period of time to become hydrated. Use of this first type of intermittent catheter may prove difficult where no clean water or wetting fluid is readily available. Moreover, catheter sterility may be compromised due to the user's handling of the catheter when wetting fluid is applied.

A second type of pre-wetted intermittent catheter is also packaged in a dry environment and contains a lubricious coating. However, the wetting fluid is positioned in a pouch or container within the catheter package itself. To hydrate the catheter, the pouch or container is opened when the user is ready for insertion. Suitable examples of such catheters are disclosed in U.S. Pat. No. 7,087,048 (the disclosure of which is incorporated herein by reference in its entirety). As with the first type, this second type may be disadvantageous because the catheter is exposed to the wetting fluid for a period of time to ensure hydration of the lubricious coating. The sterility of the catheter may also be compromised during insertion.

A third type of pre-wetted intermittent catheter is packaged in a wet environment. That is, the catheter is exposed to a wetting fluid within the catheter package, thus hydrating the coating. However, the user may have difficulty handling the catheter due to its slippery surface, and excessive or imprecise handling may result in contamination of the catheter by the user. This could then expose the user to a urinary tract infection.

Existing intermittent catheters can also drain urine into a bag. Following bladder drainage into the bag, the bag may be emptied by inverting and tearing a notch. The bag may also be sealed, for example, by knotting the open end, and then discarded into a waste receptacle. Alternatively, urine can be drained into a receptacle through the tear. Either process can be slow, messy, and/or subject to urine spills.

Non-intermittent catheterization, which is used in a hospital or nursing home setting, uses the same basic technique for insertion of the urinary tract catheter. The catheter is inserted by a nurse or other health care professional, and, it remains in the patient until bladder function can be maintained independently. When the catheter is removed, patients experience a pulling sensation and may feel some minor discomfort. If the catheter is required for an extended period of time, a long-term, indwelling catheter, such as a Foley catheter, is used. To prevent infection, it should be regularly exchanged for a new catheter every three to six weeks.

Proper catheter use can also often be determined by the length of time that the process is necessary: long-term (often called indwelling) or short-term use. In some situations, incontinent patients are catheterized to reduce their cost of care. A condom catheter, which fits on the outside of the penis using adhesive, can be used for short-term catheterization in males. However, long-term catheterization is not recommended because chronic use carries a significant risk of urinary tract infection. This risk catheterization should only be considered as a last resort for the management of incontinence where other measures have proved unsuccessful and where there is significant risk to the skin.

A catheter that is left in place for a period of time may be attached to a drainage bag to collect the urine. There are two types of drainage bags. One is a leg bag being a smaller drainage device that attaches by elastic bands to the leg. A leg bag is usually worn during the day, as it fits discreetly under pants or skirts, and is easily emptied into a toilet. The second type of drainage bag is a larger device called a down drain that may be used during the night. This device is usually hung on the patient's bed or placed on the floor nearby.

During long-term use, the catheter may be left in place the entire duration, or a patient may be instructed on a intermittent self-catheterization procedure for placing a catheter just long enough to empty the bladder and then removing it. Patients undergoing major surgery are often catheterized and may remain so for long durations. Long-term catheterization can expose patients to an increased risk of infection. Long-term catheterization as a remedy for conditions such as urinary incontinence is not appropriate, as the risks outweigh the benefits.

In males, for example, the catheter tube is inserted into the urinary tract through the penis. A condom catheter can also be used. In females, the catheter is inserted into the urethral meatus, after a cleansing using povidone-iodine. The procedure can be complicated in females due to varying layouts of the genitalia (due to age, obesity, Female genital cutting, childbirth, or other factors), but a good clinician should rely on anatomical landmarks and patience when dealing with such a patient.

Common indications to catheterize a patient include acute or chronic urinary retention (which can damage the kidneys), orthopedic procedures that may limit a patient's movement, the need for accurate monitoring of input and output (such as in an ICU), benign prostatic hyperplasia, incontinence, and the effects of various surgical interventions involving the bladder and prostate.

For some patients the insertion and removal of a catheter can cause excruciating pain, so a topical anesthetic can be used for patients of both sexes. Catheterization should be performed as a sterile medical procedure and should only be done by trained, qualified personnel, using equipment designed for this purpose. However, in the case of intermittent self catheterization, the patient can perform the procedure his/her self. If correct technique is not used, trauma may be caused to the urethra or prostate (male). A urinary tract infection or paraphimosis may also occur (male uncircumcised patient).

Particular complications of catheter use may include: urinary tract or kidney infections, blood infections (sepsis), urethral injury, skin breakdown, bladder stones, and blood in the urine (hematuria). After many years of catheter use, bladder cancer may also develop. In using indwelling (long-term) catheters, it is particularly very important to take everyday care of the catheter and the drainage bag.

Catheters come in a large variety of sizes, materials (latex, silicone, PVC, or Teflon), and types (Foley catheter, straight catheter, or coude tip catheter). In the case of internal catheters, those inserted into the urethra, the smallest size is usually recommended, although a larger size is sometimes needed to control leakage of urine around the catheter. A large size can also become necessary when the urine is thick, bloody or contains large amounts of sediment. Larger internal catheters, however, are more likely to cause damage to the urethra. Some people develop allergies or sensitivities to latex after long-term latex catheter use. In such cases, silicone or Teflon types should be used. Silver alloy coated urinary catheters may reduce infections.

Catheter diameters are sized by the French catheter scale (F). The most common sizes are 10 F to 28 F. The clinician selects a size large enough to allow free flow of urine, but large enough to control leakage of urine around the catheter. A larger size can become necessary when the urine is thick, bloody or contains large amounts of sediment. Larger catheters, however, are more likely to cause damage to the urethra. (Jeffrey A N et al., Surgery: Basic Science and Clinical Evidence Springer, 2nd ed., 2008, p. 281).

Finally, it is noted that conventional intermittent catheter are often ill-suited for those patients who self-catheterize in environs other than their homes (e.g., public restrooms). Discrete and compact packaging is important for such patients in terms of privacy, being able to carry multiple intermittent catheters on the patient's person, and to facilitate discrete disposal of the used catheters.

SUMMARY OF THE INVENTION

The present invention is directed to easy-to-use urinary catheter assemblies that eliminate or minimize at least some of the shortcomings of prior art devices. The catheter can be a single-use catheter and/or may be packaged as a single-use device. Non-limiting embodiments of the invention include one or more features described herein and/or shown in the drawings in combination with one of more prior art features discussed above.

Non-limiting embodiments of the invention provide for an easy-to-use urinary catheter assembly that provide for discrete transport and disposal and that eliminates or minimizes some of the shortcomings of conventional devices.

Non-limiting embodiments of the invention also provide for a catheter assembly comprising an inner member having a proximal end, a distal end, and a lumen configured to store a hydrating fluid and an outer member having a proximal end, a distal end, and a lumen configured to receive therein a portion of the inner member. The outer member is movable relative to the inner member at least one of between a first position preventing fluid from passing out of the at least one drainage opening from within the lumen of the inner member and a second position allowing fluid to pass out of the at least one drainage opening from within the lumen of the inner member, between a first position wherein at least one drainage opening of the outer member is closed-off by a portion of the inner member and a second position wherein at least one drainage opening of the outer member is not closed-off by the portion of the inner member, and between a first position wherein a distal opening of the inner member is closed-off by a portion of the outer member and a second position wherein the distal opening is not closed-off by the portion of the outer member.

In the first position, the outer member may substantially cover an entire visible portion of the inner member. In the second position, the distal end of the outer member may extend out past the distal end of the inner member by an amount greater than about 25% of an overall length of the outer member. In the second position, the distal end of the outer member may extend out past the distal end of the inner member by an amount greater than about 50% of an overall length of the outer member. In the second position, the distal end of the outer member may extend out past the distal end of the inner member by an amount equal to between about 50% and 90% of an overall length of the outer member.

At least the outer member may further comprise one of a hydrateable coating arranged at least on an outer surface, a lubricious coating arranged at least on an outer surface, and a hydrophilic biocompatible coating arranged at least on an outer surface.

The catheter assembly may be an intermittent catheter. Only the outer member may comprise any drainage openings. The at least one drainage opening may comprise one of at least two staggered openings, at least two generally oval-shaped openings, between 1 and 10 openings, and between 2 and 6 openings.

The outer member may further comprise a hydrateable coating arranged at least on an outer surface of the distal end of the outer member. The outer member may comprise a lubricious antimicrobial coating arranged at least on an outer surface of the distal end of the outer member.

The inner member may comprise a lubricious antimicrobial coating arranged at least on an outer surface of the distal end of the inner member. The distal end of the inner member may be at least one of configured to sealingly engage with an inner portion of the distal end of the outer member and configured to sealingly engage with an inner circumferential portion of, the distal end of the outer member so as to close-off the at least one drainage opening.

The outer member may comprise a closed distal end and one of a hydrateable coating arranged at least on a substantial portion of an outer surface, a lubricious coating arranged at least on a substantial portion of an outer surface, and a hydrophilic biocompatible coating arranged at least on a substantial portion of an outer surface.

The outer member may comprise a generally rounded and/or atraumatic closed distal tip and further comprising a plug arranged on a proximal end of the catheter assembly. The outer member may be telescopically movable and lockable in the second position. The outer member may be releasably retainable in the second position. The outer member may be non-releasably retainable in the second position. The outer member may be releasably retainable in the second position via a threaded engagement. The outer member may be lockable in the second position via a threaded engagement. The outer member may be lockable in the second position via engagement between at least one locking projection and at least one locking recess. The outer member may be releasably retainable in the second position via engagement between at least one locking projection and at least one locking recess. The outer member may be non-releasably retainable in the second position via engagement between at least one locking projection and at least one locking recess. The outer member may be non-removably connected to the inner member.

The catheter assembly may further comprise at least one of a flexible container and a pouch arranged to substantially contain therein the outer member and the inner member, and the hydrating fluid arranged in the lumen of the inner member, a flexible container and a pouch sized to accommodate movement of the outer member relative to the inner member between the first and second positions, a flexible container and a pouch comprising an expandable section, and a removably securable flexible container or pouch.

Non-limiting embodiments of the invention also provide for a method of making the catheter assembly described above, wherein the method comprises assembling the outer member onto the inner member and arranging the assembly in at least one a flexible container and a pouch.

Non-limiting embodiments of the invention also provide for a method of inserting the catheter assembly described above, wherein the method comprises moving the outer member to the second position and inserting the outer member into a user's body. The method may further comprise draining a fluid from the user's body. The fluid may be urine.

Non-limiting embodiments of the invention also provide for a catheter package comprising an inner member having a proximal end, a distal end, and a lumen configured to store a hydrating fluid, an outer member having a proximal end, a distal end, and a lumen configured to receive therein a portion of the inner member, and at least one a flexible container and a pouch arranged to substantially contain therein the outer member and the inner member. The outer member may be movable relative to the inner member at least one of between a first position preventing fluid from passing out of the at least one drainage opening from within the lumen of the inner member and a second position allowing fluid to pass out of the at least one drainage opening from within the lumen of the inner member, between a first position wherein at least one drainage opening of the outer member is closed-off by a portion of the inner member and a second position wherein at least one drainage opening of the outer member is not closed-off by the portion of the inner member, and between a first position wherein a distal opening of the inner member is closed-off by a portion of the outer member and a second position wherein the distal opening is not closed-off by the portion of the outer member.

Non-limiting embodiments of the invention also provide for a catheter package comprising a catheter assembly comprising an inner member having a proximal end, a distal end, and a lumen configured to store a hydrating fluid and an outer member having a proximal end, a distal end, and a lumen configured to receive therein a portion of the inner member. At least one a flexible container and a pouch is arranged to substantially contain therein the catheter assembly. The outer member is movable relative to the inner member and is non-removably retained thereto.

The outer member may be movable relative to the inner member at least one of between a first position preventing fluid from passing out of the at least one drainage opening from within the lumen of the inner member and a second position allowing fluid to pass out of the at least one drainage opening from within the lumen of the inner member, between a first position wherein at least one drainage opening of the outer member is closed-off by a portion of the inner member and a second position wherein at least one drainage opening of the outer member is not closed-off by the portion of the inner member, and between a first position wherein a distal opening of the inner member is closed-off by a portion of the outer member and a second position wherein the distal opening is not closed-off by the portion of the outer member.

Non-limiting embodiments of the invention also provide for a catheter assembly comprising one of at least one feature shown in the drawings and/or described in the instant application, a majority of features shown in the drawings and/or described in the instant application, any combination of plural features shown in the drawings and/or described in the instant application, and substantially all of the features shown in the drawings and/or described in the instant application.

BRIEF DESCRIPTION OF DRAWINGS OF THE EXEMPLARY EMBODIMENTS

FIG. 1 shows an intermittent elongate catheter or catheter system in a closed/retracted/original/pre-use configuration.

FIG. 2 shows the intermittent elongate catheter of FIG. 1 in an open/extended/use configuration. In this position, the hydrating fluid trapped in the inner member is free to exit from the eyelets so as to hydrate a coating of the outer member and facilitate insertion of the catheter in to a user's body.

FIG. 6 shows the catheter assembly in FIG. 1 in a packaged configuration.

FIG. 7 shows the catheter package of FIG. 6 after the user places the catheter assembly into the expanded position shown in FIG. 2. In this position, the hydrating fluid trapped in the inner member is free to exit from the eyelets, but is also contained within a pouch of the packaged catheter so as to hydrate a coating of the outer member and facilitate insertion of the catheter in to a user's body after the user removes the pouch.

Figure 8:
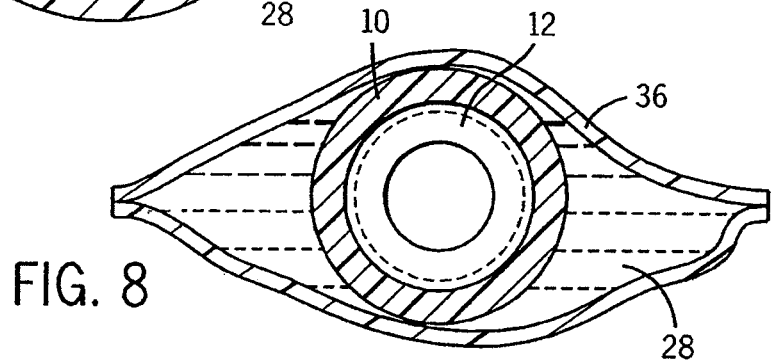

FIG. 8 shows a cross-sectional view of FIG. 7 in a distal region of the catheter package.

Figure 9:
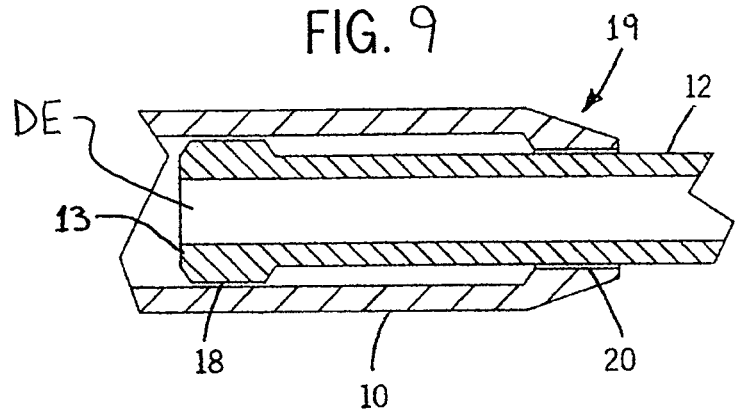

FIG. 9 shows an enlarged portion of the middle region of the catheter assembly of FIG. 2 and shows one non-limiting way in which the proximal end of the outer member can be tapered so as to facilitate removal of the catheter assembly from a user's body.

Figure 10:
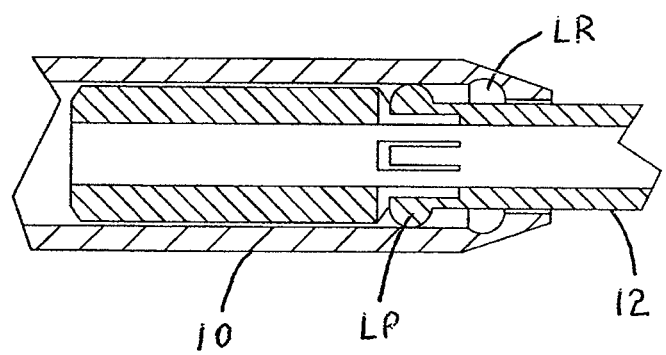

FIG. 10 shows an enlarged portion of the middle region of the catheter assembly of FIG. 2 and shows another non-limiting way in which the proximal end of the outer member can be tapered so as to facilitate removal of the catheter assembly from a user's body. This embodiment also replaces the threaded connection of FIG. 9 with a system of releasable locking projections and a locking recess. The distal end of the inner member also includes an elongated cylindrical section which is sized to close-off the eyelets and prevent leaking of the fluid inside the inner member when the catheter assembly is in a position shown in FIG. 1.

Figure 11:
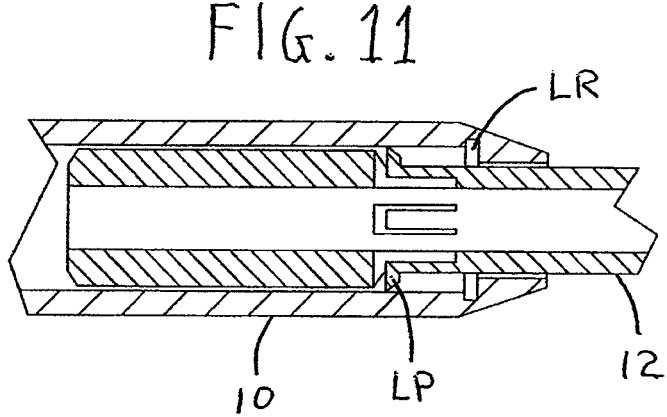

FIG. 11 shows an enlarged portion of the middle region of the catheter assembly of FIG. 2 and shows another non-limiting way in which the proximal end of the outer member can be tapered so as to facilitate removal of the catheter assembly from a user's body. This embodiment also replaces the threaded connection of FIG. 9 with a system of non-releasable locking projections and a locking recess. The distal end of the inner member also includes an elongated cylindrical section which is sized to close-off the eyelets and prevent leaking of the fluid inside the inner member when the catheter assembly is in a position shown in FIG. 1.

DETAILED DESCRIPTION OF THE EXEMPLARY EMBODIMENTS

The following description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will enable one skilled in the art to make and use the invention, and describes several embodiments, adaptations, variations, alternatives and uses of the invention, including what is presently believed to be the best mode of carrying out the invention.

As used herein, the reference terms "proximal" and "distal" (proximal being closer than distal) refer to proximity with respect to a health care professional catheterizing a patient. For example, the region or section of the catheter apparatus that is closest to the health care professional during catheterization is referred to herein as "proximal," while a region or section of the catheter apparatus closest to the patient's bladder is referred to as "distal." In the case of a self-catheterizing patient, proximal refers to a point external to the patient's body, and distal refers to a point within the patient's body (i.e., the bladder).

The catheter assemblies as described herein are discussed in the context of a urinary catheter for insertion into a bladder for drainage of urine therefrom. The instant catheter assemblies, however, may also be used for other applications not specifically mentioned herein. As such, the instant invention is not limited to urinary catheter applications.

FIGS. 1 and 2, and 6 and 7, show a non-limiting embodiment of an elongate urinary intermittent catheter assembly/catheter package of the present invention. FIGS. 1 and 6 show the catheter assembly in a closed/retracted/original/initial configuration whereas FIGS. 2 and 7 show the catheter assembly in an open/extended/using/locked configuration.

The assembly 1 shown in FIG. 1 first placed into the configuration of FIG. 2 so that the fluid trapped inside the inner member 12 can exit from the eyelets 14 of the outer member 10 and hydrate the coating of the outer member 10. The assembly 1 can then be inserted into a user's body until the distal end 16 is safely positioned in the bladder. Thereafter, the assembly 1 can be removed and discarded or placed into the position shown in FIG. 1 and then discarded. Of course, in order for the above procedure to take place in a more safe and clean environment, the procedure takes place with the catheter assembly 1 in the packaged configuration shown in FIGS. 6 and 7. The pouch 36 functions to preserve the clean environment therein and retains the hydrating fluid so that it can sufficiently coat the outer member 10 (as well as the inner member 12).

Once the catheter assembly 1 is hydrated by placing it into the configuration of FIG. 7, the pouch 36 is removed (or the distal end 16 is forced through, e.g., by puncturing, the distal end of the pouch 36) so that the assembly 1 can be inserted into the bladder to drain urine therefrom via the catheter. A substantial portion or all of the outer surface of the outer member 10 and, in embodiments, also the inner member 12 includes a lubricious coating, which can be hydrated by the hydrating fluid, to facilitate insertion of the catheter into the user's body.

With reference to FIGS. 1 and 2, the catheter assembly 1 includes an elongate inner member 12 having proximal and distal ends and a lumen arranged therein. The lumen of the inner member 12 functions as a hydrating fluid storing area (see FIGS. 3 and 4) which is substantially filed with a hydrating fluid 28. By way of non-limiting example, the hydrating fluid 28 can be a sterile wetting fluid such as, e.g., water. While the catheter assembly 1 is in the position shown in FIGS. 1 and 6, the fluid 28 remains trapped in the lumen of inner member 12. This is because the distal end of the inner member 12 sealingly engages with an internal area of the distal end 16 of the outer member 10 and also closes-off the eyelets 14, which, with the exception of the plug 30 (see FIGS. 6 and 7), provides the only way for the fluid 28 to escape from out of the lumen of the inner member 12. Once the catheter assembly 1 is placed into the position shown in FIGS. 2 and 7, the fluid 28 can substantially exit from the lumen of the inner member 12 via the eyelet openings 14 of the outer member 10. The lumen of the inner member 12 can then function in the usual manner by allowing a body fluid, e.g., urine, to pass through and/or drain out of the proximal end of the catheter assembly 1. The plug 30 can be removed before or after the catheter assembly 1 is inserted into the body. Removal of the plug 30, for example, allows urine to pass through the eyelets 14, then through member 10, then through member 12, and finally out of the member 26.

The proximal end 15 of the inner member 12 extends to a hollow fitting 22. The distal end 13 (see FIG. 9) of the inner member 12 includes an external thread 18. The elongate inner member 12 can have any size and shape typically utilized in conventional catheters such as generally cylindrical and defines an interior lumen or space which allows fluid to pass and/or drain through. In addition to the hollow fitting 22, handle/grip member 24 and a funnel 26 are arranged on the proximal end of the catheter assembly 1. The members 22, 24 and 26 can be of any type that is typically utilized in catheters. In embodiments, the funnel 26 can be connected to any type fluid collection system or bag that is typically utilized in catheters. By way of non-limiting example, the funnel 26 can be a rubber or plastic drainage funnel disposed and friction-fitted on the proximal end of the member 12. A disposable bag (not shown) may be disposed on and/or coupled to the drainage funnel 26 to collect the patient's urine. The distal end of the inner member 12 is, in embodiments, open to allow the hydrating fluid 28 exit from the lumen when the distal end is moved back away from the distal end 16 of the outer member 10. The elongate inner member 12 also, in embodiments, contains a biocompatible, hydrophillic, antimicrobial and/or lubricious coating on its outer surface (not shown).

An elongated outer member 10 is arranged on the elongate inner member 12. The outer member 10 has proximal and distal ends. The proximal end 19 (see FIG. 9) has an internal thread 20 arranged therein which can lock and/or releasably lock and/or threadably engage with the threads 18 of the inner member 12. The outer member 10 is capable of moving between the positions shown FIGS. 1 and 2 and/or FIGS. 6 and 7. A distal end 16 of the outer member 10 is closed and is, in embodiments, rounded so as to facility entry and/or prevent damage to tissue. The outer member 10 can have any size and shape, but, in embodiments, generally corresponds to that of the member 12. The outer member 10 can be generally cylindrical and defines an interior lumen or space which receives therein (with some clearance) the elongate inner member 12. The member 10 (and optionally also the inner member 12) can also be substantially transparent or translucent. The dotted lines in FIGS. 1 and 2 represent the inner and outer diameter surfaces of the member 12 and the member 10 respectively. At least the outer member 10 also, in embodiments, has a biocompatible, hydrophillic, antimicrobial and/or lubricious coating on its outer surface (not shown). The coating becomes a lubricating coating when it comes into contact with the hydrating fluid 28 and can facilitate insertion of the catheter assembly 1. The coating can also be utilized to increase drainage efficiency and reduce propensity of residual urine in the bladder after voiding.

When the user moves the catheter assembly 1 from the position shown in FIG. 1 (or more correctly from that of FIG. 6) to that shown in FIG. 2 (or more correctly to that of FIG. 7), the user can rotate inner member 12 relative to the outer member 10 (or vice versa) to cause engagement of the threads 18 and 20. This effectively locks the catheter assembly 1 in the position shown in FIG. 2 (or FIG. 7). Once the coating of the outer member 10 achieves a lubricious state, the catheter assembly 1 can be removed from the pouch 36 and inserted into, e.g., a bladder. In order that the catheter assembly 1 can then be removed in a more safe and less painful manner, the proximal end 19 of the outer member 10 can include a tapered region (see, e.g., FIG. 9).

Figure 3:
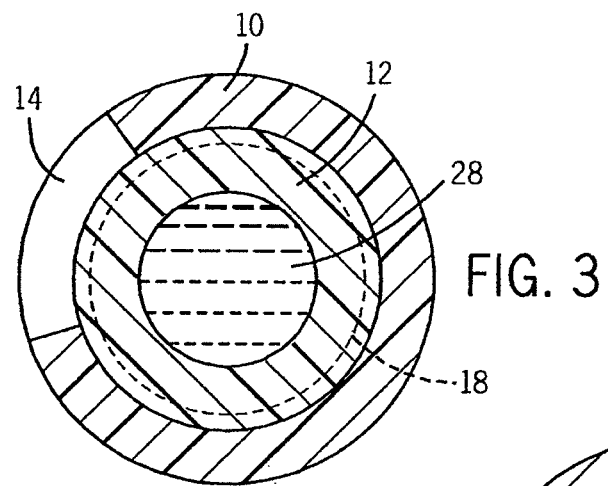
FIG. 3 shows a cross-sectional view of FIG. 1 near the distal end of the catheter assembly.

With reference to FIGS. 1, 2 and 3, it can be seen that the distal end 16 of the outer member 10 can include one or more drainage eyelet-shaped apertures or openings 14. The openings 14 can any shape or configuration typically utilized of catheters of the type disclosed herein. However, it is preferred that they be located in a distal region of the outer member 10 which allows them to be closed-off by a distal region of the inner member 12. These openings 14 allow an exiting of fluid 28 from within the lumen of the inner member 12 and entry of fluid or urine from the patient's body into the inner member 12. Thus occurs, for example, when the member 10 is inserted into a bladder after the catheter assembly 1 is moved from the position shown in FIG. 1. The plurality of apertures 14 can also provide enhanced flexibility at the distal end of the member 10, which makes the catheter more comfortable for the patient. The eyelets or openings 14 may be of any suitable size, shape, configuration and/or number so as to provide for entry of the patient's urine upon insertion into the patient's urethra, i.e., generally the first third of the urethra. In the closed/initial configuration shown in FIG. 1, the eyelets 14 are closed off by virtue of the distal end 13 of the inner member 12 being in a position which closes-off all of the openings 14. In this way, the outer surface of the inner member 12 closes-off and substantially seals the eyelets or openings 14. This sealing can occur using the frictional engagement between an inside diameter of the outer member 10 and an outer diameter of the member 12. A dual system of sealing can be provided by an annular or axial sealing engagement between the distal end 13 of the inner member 12 and the distal end 16 of the outer member 10, as well as a circumferential sealing engagement between the distal region of the inner member 12 and the distal region of the outer member 10 (which functions to close-off the openings 14). A lubricious coating can also be arranged on an inside diameter of the outer member 10 and/or an outer diameter of the member 12 to, among other things, facilitate the relative movement of the member 10 relative to the member 12 between the positions shown in FIGS. 1 and 2 or FIGS. 6 and 7.

Figure 4:
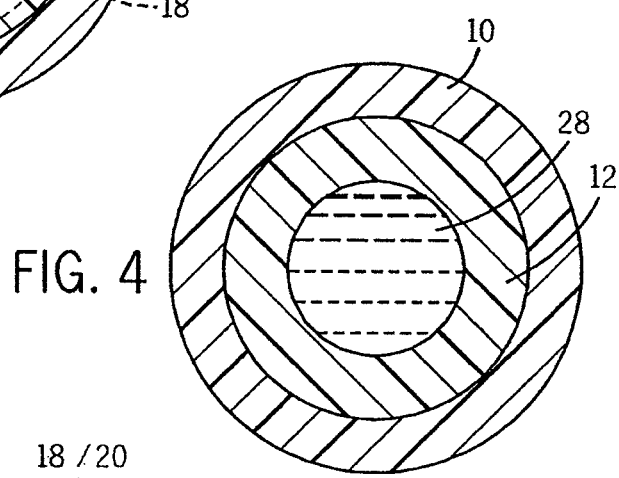
FIG. 4 shows a cross-sectional view of FIG. 1 near the proximal end of the catheter assembly.

With reference to FIG. 3, it can be seen that the opening 14 is closed-off by the distal region of the inner member 12 and the fluid 28 is retained and/or trapped in the lumen of the inner member 12. FIG. 4 shows that the fluid 28 extends essentially from one end of the inner member 12 to another and substantially fills the lumen thereof.

Figure 5:
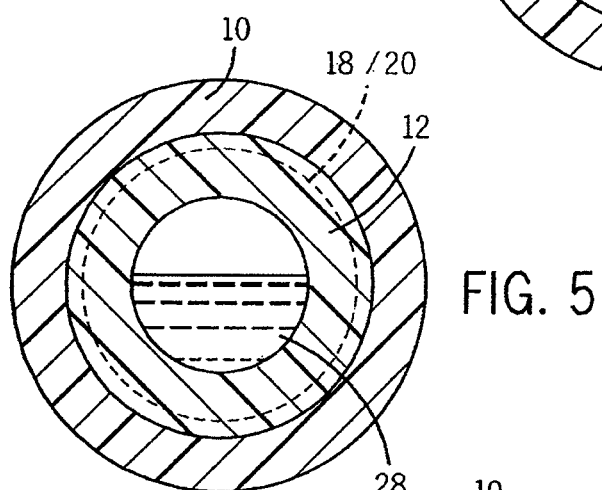
FIG. 5 shows a cross-sectional view of FIG. 2 in a middle region of the catheter assembly.

With reference to FIG. 5, it can be seen that after the catheter assembly 1 is placed into the position of FIG. 2 and the opening 14 no longer closed-off by the member 12, some or most of the fluid 28 previously trapped in the lumen of the inner member 12 has now exited via the openings 14. FIG. 8 shows that substantially all of the fluid 28 has exited from the lumen of the inner member 12 (via the openings 14) and has gone into the pouch 36 whereby the fluid 28 functions to hydrate the coating of the member 10 (and in embodiments also member 12). The pouch 36 allows the fluid to slosh around the catheter assembly 1 so as to hydrate its coating(s). It also functions to retain the fluid 28 and to preserve the clean environment around the catheter assembly 1, or at least the parts thereof which will be inserted into a user or patient. It additionally also serves as a discardable package so as to make clean up less messy for the user, i.e., to the extend that some of most of the fluid 28 remains in the pouch 36 after the user inserts the catheter assembly 1 into the bladder, such fluid can be contained for disposal.

With reference to FIGS. 6 and 7, it can be seen that the catheter assembly of FIGS. 1 and 2 is, in embodiments, formed as a catheter package 40. The catheter package 40 utilizes the catheter assembly 1 of FIGS. 1 and 2, and a packaging pouch 36. The pouch 36 is, in embodiments, made of a flexible material and has a closed distal end, an open proximal end, and an expandable section 34. The material of the pouch 36 should be sufficiently flexible to allow the user to lock the catheter assembly 1, e.g., via a twisting motion causing engagement of the threads 18/20, into the extended position. With the catheter assembly 1 in the closed/retracted configuration (FIG. 1), it can be packaged in the sterile and flexible protective pouch 36, which is also in a retracted configuration. The pouch 34 is constructed from suitable materials that are at least substantially impermeable to moisture and airborne contaminants. The expandable section 34 allows the pouch 36 to move from the position of FIG. 6 to the position of FIG. 7 without causing a tearing of the pouch 36. The open end of the pouch 36 is configured to be sealingly and non-movably retained to a proximal portion of the catheter assembly 1. By way of non-limiting example, the open end of the pouch 36 is sealingly removably secured to the funnel portion 26 of the catheter assembly 1. Of course, it can also be sealing removably connected to other portions such as, e.g., portions 22 and/or 24. By way of non-limiting example, this sealingly removably secured connection can occur by way of a band 32 which is, in embodiments, removable and/or is capable of breaking and/or is a frangible band. The band 32 is, in embodiments, removable so as to allow the user to remove the pouch 36 from the catheter assembly 1 after the catheter package 40 is moved from the position shown in FIG. 6 to that shown in FIG. 7, and after the catheter assembly 1 is deemed to be sufficiently hydrated by the fluid 28. Although not shown, it is possible to make the distal end of the pouch 36 tearable or puncturable by the distal end 16 of the outer member 10 so that the user can force the distal end 16 of the outer member 10 through the distal end of the pouch 36.

FIGS. 9-11 show non-limiting alternative configurations for the system that can lock and/or retain the catheter assembly 1 in the position shown in FIGS. 2 and 7. In FIG. 9, the external threads 18 of the inner member 12 can threadably engage the internal threads 20 of the Outer member 10. This can occur by, e.g., a quarter turn twisting action between the members 10 and 12. A distal opening DE is also shown in FIG. 9. The end of the inner member 12 is such that when placed into contact with in inner portion of distal end 16, the opening DE is essentially sealed or closed off by the outer member 10. In FIG. 10, releasable locking projections LP of the inner member 12 can releasably engage with an internal locking recess LR of the outer member 10. This can occur by, e.g., an axial movement action between the members 10 and 12. The distal end of the inner member 12 also includes an elongated cylindrical section which is sized to close-off the eyelets 14 and prevent leaking of the fluid 28 inside the inner member 12 when the catheter assembly 1 is in a position shown in FIG. 1. As demonstrated by FIGS. 10 and 11, instead of threads (see FIG. 9), the outer member 10 and inner member 12 may be assembled by a suitable friction fit. This connection can thus utilize a threaded engagement, protrusions, grooves, detents, recesses, or other like securing/locking structures. Extension of the catheter assembly by telescopically actuating the member 10 opens the eyelet apertures 14 providing for liquid communication between the interior and exterior of the catheter assembly.

The inner member 12 and outer member 10 may have a round cross-sectional shape, an oval cross-sectional shape, or any other cross-sectional shape that may facilitate insertion into the body of a user/patient, and, in particular, into the bladder of the user/patient through the urethra. The member 10 (in accordance with various embodiments), and optionally also member 12, can, in embodiments, contain a biocompatible lubricious and/or antimicrobial coating on at least an outer surface thereof. Suitable non-limiting examples of such lubricious and antimicrobial coatings are disclosed in U.S. Pat. Nos. 4,585,666; 5,558,900; 5,077,352; 5,179,174; 6,329,488 (suitable for, e.g., polysiloxane substrates); U.S. Pat. Nos. 6,716,895; 6,949,598; and U.S. Patent Application Publication No. 2004/0116551, and, WO 2007/050685, each of which is incorporated by reference in its entirety.

The antimicrobial agent used on the catheter may be one listed in an over the counter (OTC) monograph. Biocompatible coatings conform with the following tests: mucosal irritation, sensitization, cytotoxicity, acute systemic toxicity, and implantation. ("Tripartite Biocompatibility Guidance for Medical Devices," DSMA (Apr. 24, 1987) (Updated May 21, 1996)). The purpose of the wetting fluid is to maintain hydration of the lubricious coating such that upon insertion of the conduit into a user, at least an outer portion thereof is extremely slippery, facilitating insertion.

The members 10, 12 may, in embodiments, be constructed from a suitable polymeric material, such as polyethylene or polypropylene. The components of the catheter disclosed herein can also be made from various well-known materials. For example, the portions of the assembly other than the members 10, 12 can be made of polyvinyl propylene, polyvinyl chloride, polyethylene, and other types of suitable polymeric materials. The components can be molded or extruded according to well-known manufacturing techniques.

Materials commonly used to make the members 10 and 12 include, but are not limited to natural rubber latexes (available, for example, from Guthrie, Inc., Tucson, Ariz.; Firestone, Inc., Akron, Ohio; and Centrotrade USA, Virginia Beach, Va.), silicones (available, for example, from GE Silicones, Waterford, N.Y., Wacker Silicones, Adrian, Mich.; and Dow Corning, Inc., Midland, Mich.), polyvinyl chlorides (available, for example, from Kaneka Corp., Inc., New York, N.Y.), polyurethanes (available, for example, from Bayer, Inc., Toronto, Ontario, Rohm & Haas Company, Philadelphia, Pa.; and Ortec, Inc., Greenville, S.C.), plastisols (available, for example, from G S Industries, Bassett, Va.), polyvinyl acetate, (available, for example from Acetex Corp., Vancouver, British Columbia) and methacrylate copolymers (available, for example, from Heveatex, Inc., Fall River, Mass.). Natural rubber latexes, polyurethanes, and silicones are preferred materials. Any combination of the foregoing materials may also be used in making catheters. In one embodiment, a rubberize layer that includes latex and a methacrylate is used with build up and finish layers that include latex but not methacrylate. In another embodiment, a polyurethane rubberize layer is used with latex build up and finish layers. In another embodiment, a polyvinyl acetate and latex rubberize layer is used with latex build up and finish layers. Each of the foregoing embodiments in which specific Young's Modulus values are specified may be used with any material.

The urinary catheter, and in particular, at least member 10, of the present invention can be manufactured by a variety of well-known methods. For example, according to various embodiments, the catheter is manufactured by dipping. An elongated rod or "form" is dipped into a first liquid coating material to form a layer of coating material on the form. The form has the shape and dimensions of the lumen of the catheter. This first coating layer forms the inner or rubberize layer of the catheter. Once the first layer has dried, the form is then dipped into a second coating material to build up an intermediate or build up layer. Multiple dips into the second coating material may be desirable to build up an intermediate layer of appropriate thickness. The build up layer is then dried. The finish layer is applied with a subsequent dip and is dried. The catheter may be stripped from the form, and eyelets may then be formed thereon. Further manufacturing steps may be found in U.S. 2004/0133156, the disclosure of which is incorporated by reference herein.

Each member 10 and 12 may, in embodiments, be in the range of, for example, about 4 cm to about 9 cm (providing a catheter assembly 1 having a maximum length of between about 8 cm and 18 cm), and, it may have an elliptical cross-sectional shape similar to the shape of the male urethra. Different lengths, sizes (e.g., diameter, width, etc.), and configurations are possible for the catheter, depending on the user's anatomy. For female users, the insertable length of the catheter assembly 1 may range from 40 to 100 mm, for example 50 to 80 mm, such as 55 to 75 mm. For male users, the insertable length can range from 170 to 260 mm, such as 190 to 240 mm, for example 230 mm. The tip design can vary according to the needs of a user, for example, the catheters disclosed herein can be provided with a coude tip. The catheter may have a round or substantially round cross-sectional shape, an oval cross-sectional shape, or any other cross-sectional shape that may facilitate insertion into the body of a user/patient, and in particular, into the bladder of the user/patient through the urethra. According to various embodiments, the shape of the catheter can also be variable along its length.

This invention has been described and specific examples of the invention have been portrayed. While the invention has been described in terms of particular variations and illustrative figures, those of ordinary skill in the art will recognize that the invention is not limited to the variations of figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A catheter assembly comprising:
    an inner member having a proximal end, a distal end, and a lumen;
    a hydrating fluid stored in the inner member lumen in a first catheter assembly position; and
    an outer member designed for insertion into a urethra of a patient surrounding the inner member in the first catheter assembly position, the outer member having a proximal end, a distal end, a lumen, and at least one drainage opening, wherein the outer member is movable relative to the inner member between the first catheter assembly position preventing fluid from passing out of the at least one drainage opening from within the lumen of the inner member and a second catheter assembly position allowing fluid to pass out of the at least one drainage opening.

2. The catheter assembly of claim 1, wherein, in the first catheter assembly position, the outer member covers an entire visible portion of the inner member.

3. The catheter assembly of claim 1, wherein, in the second catheter assembly position, the distal end of the outer member extends past the distal end of the inner member by an amount greater than about 25% of an overall length of the outer member.

4. The catheter assembly of claim 1, wherein, in the second catheter assembly position, the distal end of the outer member extends past the distal end of the inner member by an amount greater than about 50% of an overall length of the outer member.

5. The catheter assembly of claim 1, wherein, in the second catheter assembly position, the distal end of the outer member extends past the distal end of the inner member by an amount equal to between about 50% and 90% of an overall length of the outer member.

6. The catheter assembly of claim 1, wherein the outer member further comprises a coating arranged on an outer surface including at least one of:
    a hydrateable coating;
    a lubricious antimicrobial coating; and
    a hydrophilic biocompatible coating.

7. The catheter assembly of claim 1, wherein the at least one drainage opening comprises one of:
    at least two staggered openings;
    at least two generally oval-shaped openings; and
    between 2 and 6 openings.

8. The catheter assembly of claim 1, wherein the inner member comprises a lubricious antimicrobial coating arranged at least on an outer surface of the distal end of the inner member.

9. The catheter assembly of claim 1, wherein the outer member comprises a generally rounded and/or atraumatic closed distal tip and further comprising a plug arranged on a proximal end of the catheter assembly.

10. The catheter assembly of claim 1, wherein the outer member is telescopically movable and lockable in the second catheter assembly position.

11. The catheter assembly of claim 1, wherein the outer member is releasably retainable in the second catheter assembly position via a threaded engagement.

12. The catheter assembly of claim 1, wherein the outer member is releasably retainable in the second catheter assembly position via engagement between at least one locking projection and at least one locking recess.

13. The catheter assembly of claim 1, further comprising at least one of:
    a flexible container arranged to substantially contain therein the outer member and the inner member;
    a flexible container sized to accommodate movement of the outer member relative to the inner member between the first and second catheter assembly positions;
    a flexible container comprising an expandable section; and
    a removably securable flexible container or pouch.

14. The catheter assembly of claim 1, wherein the outer member includes a hydrophillic coating, and wherein when the outer member is in the second catheter assembly position, the hydrating fluid is allowed to pass out of the at least one drainage opening to contact the hydrophillic coating and form a lubricating coating on the outer member.

* * * * *